United States Patent [19]
Jayasuriya et al.

[11] Patent Number: 5,946,638
[45] Date of Patent: Aug. 31, 1999

[54] REGIOSELECTIVE NITRATION OF AROMATIC COMPOUNDS AND THE REACTION PRODUCTS THEREOF

[76] Inventors: Keerthi Jayasuriya, 56 Sparrow Cir., Newton, N.J. 07860; Reddy Damavarapu, 14 Canterbury Ln., Hackettstown, N.J. 07840

[21] Appl. No.: 09/131,064

[22] Filed: Aug. 7, 1998

Related U.S. Application Data

[63] Continuation-in-part of application No. 08/919,069, Aug. 22, 1997, abandoned.

[51] Int. Cl.$^6$ .................................................. C07C 205/00
[52] U.S. Cl. ........................................... 568/927; 568/936
[58] Field of Search ..................................... 568/927, 936

[56] References Cited

FOREIGN PATENT DOCUMENTS 63303957  12/1988  Japan .

OTHER PUBLICATIONS

Kwok J. Thmas et al. J. Org. Chem. 1994, 59, 4939–4942.
Smith Keith et al. Chem. Commun. Cambridge, 1996, 4, 469–470.
Gaudreault J. et al. Journal of Parmaceutical Science, 1988, 77 (2), 185–187.
Japanese Abstract (JP 51019734 A) WPIDS data base, Jan. 09, 1993.

*Primary Examiner*—Paul J. Killos
*Assistant Examiner*—J. Parsa

[57] ABSTRACT

A method is described for the regioselective nitration of substituted aromatic compounds. The reaction is effected by heating the aromatic compound to a temperature within the range of 70–90° C. in the presence of a solid zeolite catalyst and adding concentrated nitric acid to the heated mixture, the concentration of the acid ranging from 90–98%, by weight.

13 Claims, No Drawings

REGIOSELECTIVE NITRATION OF AROMATIC COMPOUNDS AND THE REACTION PRODUCTS THEREOF

CROSS REFERENCE TO RELATED APPLICATION

This application is a continuation-in-part of our application, Ser. No. 08/919,069, filed Aug. 22, 1997 now abandoned.

STATEMENT OF GOVERNMENT INTEREST

The United States of America has certain rights and licenses in this invention.

SUMMARY OF THE INVENTION

The present invention relates to the regioselective nitration of substituted aromatic compounds with concentrated nitric acid as the nitrating agent and a solid, small pore size, acidic zeolite as a catalyst. More particularly, the present invention relates to a process which tends to produce isomers of the substituted aromatic compound that will have the nitro substituent at the para position. The selectivity for the production of the para isomer will concomitantly reduce the proportion of ortho isomer. Furthermore, under the conditions of the reaction of this invention, the meta isomer and other by-products are produced in very small amounts. It is desirable to reduce the amount of such materials to essentially 0%.

The reaction product in accordance with the invention will be predominantly the para substituted isomer. In some circumstances, the product will be essentially 100% para isomer. The reaction products having small ortho contents can themselves be used as feedstocks. Additionally, the composition of the reaction products is such that it lends itself to further separation into the individual components.

One particular application of the invention is the regioselective nitration of substituted aromatic hydrocarbons such as toluene to nitrotoluenes. Another application of the invention is the regioselective nitration of substituted aromatic compounds in which the substituent is an electron withdrawing group which uses the mesomerism with the aromatic ring to activate the ring and establish ortho and para directed sites.

Exemplary electron-withdrawing groups of this type are oxygenated alkyls and halogens. Preferred examples of compounds that are suitable for nitration in this process are anisole and chlorobenzene.

The invention relates to novel reaction products which have a major proportion of para isomer and a minor proportion of ortho isomer, the proportion of para isomer ranging from about 80%, by weight, up to about 100%, by weight, para isomer. The invention also is directed to novel separation techniques for such reaction products and the use of these reaction products as feedstocks in other chemical processes. For example, nitrotoluenes can be nitrated to dinitrotoluenes. In turn, the dinitrotoluenes can be nitrated to trinitrotoluene. Dinitro toluene may also be converted to toluene diisocyanate (TDI) which is the feedstock for the polyurethanes. Nitro anisole may be reduced to its corresponding amine for use as an intermediate in the preparation of pharmaceuticals and dyestuffs. The same can be done with nitrochlorobenzene.

FIELD OF THE INVENTION

Nitration reactions of substituted aromatic compounds are important for the industrial production of a wide variety of essential chemical intermediates, high value commercial compounds such as p-nitrochlorobenzene and end products, including high energy explosives such as 2,4,6-trinitrotoluene (TNT).

For the nitration of aromatic compounds, especially toluene, the most widely used nitrating agents are mixtures of concentrated $HNO_3$ and $H_2SO_4$ as described by Olah, Malhotra and Narang, "Nitrations", VCH Publications, New York, (1989) at page 5. These nitration reactions are conducted under homogeneous conditions which are very corrosive and which involve serious environmental problems in the methods and costs of disposal of the spent mixed acids. These reactions also have the problem of poor distribution of isomers in the reaction products. In particular, the meta isomer is formed in an amount of about five percent. This causes severe problems because it requires the isolation and disposal of this unwanted by-product A variety of systems have been attempted for the nitration of toluene. Smith has reported (Smith, K. Fry, K. Tetrahydon Lett., 1989, 30, 5333) a nitration of toluene which uses large pore-size mordenite catalyst and benzoyl nitrate as the nitration source.

The reaction product has a controlled distribution of isomers. There are also problems in this process with the making and handling of benzoyl nitrate. There is a strong tendency toward decomposition in moisture and air. In addition, the benzoic acid by-product requires removal with caustic aqueous extraction. Lazlo has reported (Cornelis, A.; Delaude, L.; Gerstmans, A.; Lazlo, P., Tetrahedron Lett., 1988, 29, 5657) a nitration of toluene using a clay catalyst, $Cu(NO_3)_2$ and acetic anhydride. The reaction product has about 1% meta isomer. To achieve such selectivity requires high dilution of reagents, such as 1 ml. of toluene in 2 liters of $CCl_4$. The high cost of copper nitrate would make large scale-up processes impractical.

A patent issued to Russian researchers (USSR, SU 1, 759,833,1992) generally describes a nitration of toluene with a solid zeolite catalyst, ZSM-11, and some form of nitric acid. Kwok et al., (J. Org. Chem., Vol. 59, 4939–4942, 1994) describe the nitration of toluene with a solid zeolite ZSM-5 catalyst and alkyl nitrates as nitrating agents.

DETAILED DESCRIPTION OF THE INVENTION

The present invention relates to the regioselective nitration of substituted aromatic compounds with concentrated nitric acid and a solid acidic zeolite catalyst of small pore size. The aromatic compound is substituted with at least one ring activating, ortho and para directing group. The preferred substituted aromatic compounds are members selected from alkylated aromatics, halogenated aromatics and oxygenated aromatics. The alkyl group may be methyl, ethyl, propyl or isopropyl. The preferred alkylated aromatics are toluene, ethyl benzene and cumene. As discussed previously, the group may be electron withdrawing if it also will form mesomeric bonding with the aromatic ring. The mesomeric bonding causes the ortho and para directing effect in the ring. Examples are oxygenated alkyls and halogens. When the substituents are oxygenated groups, they may be alkoxy or acyloxy. Preferred members of this group are anisole and 4-phenyl butyric acid. When the groups are halogen, the preferred members are chlorine and bromine. The reaction product will have an isomer distribution with a very high para isomer distribution, a small ortho content and a very low meta isomer content. It is preferred to have essentially 100% of the isomers in the para form.

The nitration process of the invention is very selective and uses mild conditions. The process features high yields of the para isomer; the ortho isomer will be produced in relatively low amounts and in some cases there will be none. The meta isomer will be in very low even negligible amounts. The present invention is directed to a method for the nitration of substituted aromatics such as toluene which avoids producing large amounts of environmentally hazardous materials as by-products.

The nitrating agent employed in the practice of the present invention is concentrated nitric acid. Although the term "concentrated nitric acid" is often used to describe a composition having at least about 70%, by weight, nitric acid, remainder water, it has been determined that the range of concentration required in the practice of the invention is from 90–98%. Concentrated nitric acid has been found useful herein because it is relatively inexpensive and due to its satisfactory yields and selectivity. It has been found that as the concentration of nitric acid decreases, the concentration of water in the nitric acid increases so resulting in the binding of the zeolite catalyst with water and a reduction of its catalytic activity. Accordingly, in the practice of the present invention, it has been unexpectedly found that heating to a temperature within the range of 70–90° C. enhances the yield due to increased catalytic activity as a result of the elimination of water.

The zeolite catalysts used in the practice of the invention are synthetic aluminosilicate compounds having a crystalline framework with well defined pore and cage structures. The basic structural units consist of silicon and aluminum atoms that are tetrahedrally coordinated with four oxygen atoms. Each polyhedron has a rigid geometric form and the way these polyhedron forms are connected determines the pore size of the channels in the crystal lattice. In accordance with the present invention, the pore size of the zeolite catalyst should be in the range of 5 to 5.5 A. The pore size of the zeolite catalyst has been found to play a significant role in controlling the isomer distribution of products in the nitration of substituted aromatic compounds with concentrated nitric acid. It has been observed in ZSM-5 that the para nitro isomer of the substituted compound is formed in more significant amounts as compared with conventional electrophilic nitration methods. By contrast, it appears that the use of larger pore size zeolites or multi-channel, cross network zeolites is ineffective in controlling the isomer distribution, particularly the meta isomer, of the mononitrotoluene isomer products from the nitration of toluene. The best isomer distribution of mononitrotoluene reaction products is obtained by using a zeolite catalyst such as ZSM-5 having a pore size from about 5 to 5.4 A. Several H-ZSM-5 zeolite materials with different Si/Al ratios have been investigated to determine the most suitable catalyst composition to optimize the desired isomer distribution in the reaction products. The range of Si/Al ratio is from about 120 to about 1000. The use of this catalyst is one factor that controls the isomer distribution to reduce the undesirable meta isomer and increase the desired para-nitrotoluene isomer significantly.

The practice of the present invention will be more fully understood by reference to the following examples which have been set forth solely for purposes of exposition and are not to be construed as limiting. The ZSM-5 catalyst in the protonated form, a white powder, had a ratio of $SiO_2/Al_2O_3$ (Si/Al) of 1000 unless otherwise noted below. The materials were obtained from Degussa Corporation, Fort Lee, N.J. and PQ Corporation, Valley Forge, Pa.

Nitration reactions were performed in a round bottom, flask using a Teflon coated magnetic spin bar and in air unless otherwise noted. Generally, the reaction products were slurries of solid para isomer crystals in a liquid phase of ortho isomers. The products were separated by fractional distillation into the pure components. The product distribution for each reaction was determined by gas phase chromatography using a Hewlett Packard 5890 unit and a packed column 1m by 0.533 mm capillary column. GC/MS was done with a Saturn 4D Spectrometer. The instruments were calibrated with pure reference samples.

EXAMPLE A

A mixture of 50 ml. of toluene and 25 g of H-ZSM-5 having a $SiO_2/Al_2O_3$ of 1000 was placed in a three neck 250 ml. flask, stirred and heated to 90° C. 1.70 gms of 90% HNO3 solution was added to the heated mixture dropwise over a 2 minute period. The original mixture was light tan and became an orange color as the reaction proceeded. The mixture was stirred for 4 hours and the temperature was kept between 90–95° C. At the conclusion of the experiment the flask was cooled to touch and the catalyst and solution were separated by filtration through sintered glass funnel with medium porosity. The volatile components, primarily toluene, were removed from the filtrate under reduced pressure. The remaining residue was a slurry of well defined crystals that were essentially mononitrotoluenes in the amount of 1.43 g or 43% based on the theoretical yield from nitric acid. the ratio of isomers for the mononitrotoluene was 83% para, 17% ortho and trace amounts (0.19%) of meta.

EXAMPLE B

A mixture of 50 ml. of toluene and 35 g of H-ZSM-5 having a SiO2/Al2O3 ratio of 1000 was placed in a three neck 250 ml. flask, stirred and heated to 100° C. Then, 1.46 gms of 90% HNO3 was added to the heated mixture dropwise over a 2 minute period. The original mixture was light tan and became an orange color as the reaction proceeded. The mixture was then stirred for 4 hours and the temperature kept between 100–105° C. At the conclusion of the experiment, the flask was cooled to the touch and the catalyst and solution were separated by filtration through sintered glass funnel with medium porosity. The volatile components, primarily toluene, were removed from the filtrate under reduced pressure. The remaining residue was a slurry of well defined crystals that are essentially mononitrotoluenes in the amount of 1.47 g or 51%. The ratio of isomers for the mononitrotoluenes was 80% para, 20% ortho and a trace amount of meta (0.013%).

EXAMPLE C

A mixture of 50 ml. of toluene and 35 g of H-ZSM-5 having a $SiO_2/Al_2O_3$ of 1000 was placed in a three neck 250 ml. flask, stirred and heated to 100° C. Then, 2.21 gms of 90% $HNO_3$ was added to the heated mixture dropwise over a 2 minute period. The original mixture was light tan and became an orange color as the reaction proceeded. The mixture was stirred for 4 hours and the temperature was kept between 100–105° C. At the conclusion of the experiment, the flask was cooled to the touch and the catalyst and solution were separated by filtration through a sintered glass funnel with medium porosity. The volatile components, primarily toluene, were removed from the filtrate under reduced pressure. The remaining residue was a slurry of well defined crystals that were essentially mononitrotoluenes in the amount of 2.02 g or 47%. The ratio of isomers for the mononitrotoluenes was 86% para, 14% ortho and trace amounts of meta (0.013%).

EXAMPLE D

A mixture of 50 ml of toluene and 35 g of H-ZSM-5 having a $SiO_2/Al_2O_3$ of 1000 was place in a three neck 250 ml. flask, stirred and heated to 100° C. Then, 2.95 gms of 90% HNO3 was added to the heated mixture dropwise over a 2 minute period. The original mixture was light tan and became an orange color as the reaction proceeded. The mixture was stirred for 4 hours and the temperature was kept between 100–105° C. At the conclusion of the experiment, the flask was cooled to the touch and the catalyst and solution were separated by filtration through a sintered glass funnel with medium porosity. The volatile components, primarily toluene, were removed from the filtrate under reduced pressure. The remaining residue was a slurry of well defined crystals that were essentially mononitrotoluenes in the amount of 2.46 g or 43%. The ratio of isomers for the mononitrotoluenes was 83% para, 17% ortho and trace amounts of meta (0.01%).

EXAMPLE E

A mixture of 50 ml of toluene and 35 g of H-ZSM-5 having a $SiO_2/Al_2O_3$ of 1000 was placed in a three neck 250 ml. flask, stirred and heated to 100° C. Then, 4.39 gms of 90% HNO3 was added to the heated mixture dropwise over a 2 minute period. The original mixture was light tan and became an orange color as the reaction proceeded. The mixture was stirred for 4 hours and the temperature was kept between 70–75° C. At the conclusion of the experiment, the flask was cooled to the touch and the catalyst and solution were separated by filtration through a sintered glass funnel with medium porosity. The volatile components, primarily toluene, were removed from the filtrate under reduced pressure. The remaining residue was a slurry of well defined crystals that were essentially mononitrotoluenes in the amount of 4.05 g or 47%. The ratio of isomers for the mononitrotoluenes was 60% para, 38% ortho and 1.6% meta.

EXAMPLE F

A mixture of 80 ml of ethylbenzene and 30 g of H-ZSM-5 having a $SiO_2/Al_2O_3$ of 1000 was placed in a three neck 250 ml. flask, stirred and heated to 90° C. Then, 2.25 gms of 90% HNO3 was added to the heated mixture dropwise over a 2 minute period. The original mixture was light tan and became an orange color as the reaction proceeded. The mixture was stirred for 4 hours and the temperature was kept between 90–95° C. At the conclusion of the experiment, the flask was cooled to the touch and the catalyst and solution were separated by filtration through a sintered glass funnel with medium porosity. The volatile components, primarily ethylbenzene, were removed from the filtrate under reduced pressure. The remaining residue oil was analyzed by GC/MS technique and found to be essentially 100% ethylbenzene in the amount of 2.75 g or 56% yield.

EXAMPLE G

A mixture of 100 ml of chloroform, 30 g of H-ZSM-5 having a $SiO_2/Al_2O_3$ of 1000 and 0.78 g (0.0047 mol) of 4-phenylbutyric acid was placed in a three neck 250 ml. flask, stirred and heated to 80° C. Then, 2.25 gms of 90% HNO3 was added to the heated mixture dropwise over a 2 minute period. The original mixture was light tan and became an brown color as the reaction proceeded. The mixture was stirred for 20 hours and the temperature was kept between 80–85° C. At the conclusion of the experiment, the flask was cooled to the touch and the catalyst and solution were separated by filtration through a sintered glass funnel with medium porosity. The volatile components were removed from the filtrate under reduced pressure. Yellow crystals were recovered and analyzed by GC-MS technique to contain 90% of 4-(4-nitrophenyl)butyric acid and 10% of 4-(2-nitrophenyl) butyric acid and a total yield of about 50%.

EXAMPLE H

A mixture of 40 ml of anisole and 30 g of H-ZSM-5 having a $SiO_2/Al_2O_3$ of 1000 was placed in a three neck 250 ml. flask and stirred. Then, 2.25 gms of 90% HNO3 was added to the mixture dropwise over a 2 minute period. The resulting mixture was then heated to 80° C. The original mixture turned to a violet color as the reaction proceeded. The mixture was stirred for 4 hours and the temperature was kept between 75–80° C. At the conclusion of the experiment, the flask was cooled to the touch and the catalyst and solution were separated by filtration through a sintered glass funnel with medium porosity. The volatile components, primarily anisole, were removed from the filtrate under reduced pressure. The remaining residue was analyzed by GC/MS and was found to be essentially 100% para-nitromethoxybenzene in the amount of 2.45 g or 51% yield.

EXAMPLE I

A mixture of 40 ml of isopropylbenzene (cumene) and 15 g of H-ZSM-5 having a $SiO_2/Al_2O_3$ of 1000 was placed in a three neck 250 ml. flask and stirred. Then, 2.25 gms of 90% $HNO_3$ was added to the mixture dropwise over a 2 minute period. The resulting mixture was then heated to 80° C. The original mixture turned to an orange color as the reaction proceeded. The mixture was stirred for 4 hours and the temperature was kept between 75–80° C. At the conclusion of the experiment, the flask was cooled to the touch and the catalyst and solution were separated by filtration through a sintered glass funnel with medium porosity. The volatile components, primarily isopropylbenzene, were removed from the filtrate under reduced pressure. The remaining residue was analyzed by GC/MS and was found to be essentially 100% para-nitroisoproplybenzene in the amount of 4.00 g or 59% yield.

EXAMPLE J

This example illustrates the nitration of chlorobenzene with concentrated nitric acid in the presence of ZSM-5 zeolite catalyst having a Si/Al ratio of 280. 40 ml of chlorobenzene was mixed with 5 g of H-ZSM-5 catalyst in a three neck, round bottom flask and stirred. Then, 2.67 gms of 90% $HNO_3$ was added to the mixture at room temperature. The mixture was then heated to 100° C. The original mixture turned to a bright yellow color as the reaction proceeded. The reaction temperature was kept between 90–100° C. degrees C over a reaction time of 8 hours. The flask was cooled and the zeolite catalyst and solution were separated by filtration through sintered glass filters of medium porosity. The volatile components, primarily chlorobenzene, were removed from the filtrate under reduced pressure. The remaining residue was analyzed by GC/MS and was found to be essentially 100% para-nitrochlorobenzene in the amount of 5.98 g or 96% yield based on the nitric acid.

The reaction products having the nitro groups on the substituted aromatics are capable of being used as intermediates for dyestuffs and pharmaceuticals and for additives in rubbers and plastics. One application is to convert the nitro group to an amine group to obtain the amine substituted aromatic compound.

As can be seen from the foregoing examples, the catalytic nitration system having a zeolite catalyst with small pore size, H-ZSM-5 ($SiO_2/Al_2O_3$ of 1000) and concentrated nitric acid can selectively nitrate substituted aromatic compounds. The nitro group is introduced regioselectively at the para position. The reaction product contains at least a predominate proportion of the para isomer. The ortho isomer is present in at most low concentrations and the meta isomer can be eliminated. In the case of toluene, the nitration can produce at least about 80–90% of the para isomer. The remaining product is the ortho isomer. Upon removal of all volatile components, a very small amount of meta isomer was found in the mixture. The H-ZSM-5 is a solid catalyst which eliminates the use of corrosive acids that are generally used in the nitration process.

It has been found that the isolable yields are greater than a H-ZSM-11 and benzoyl nitrate system that produces similar selectivity for the para isomer. The process of this invention operates at mild conditions, e.g. optimum temperature ranges from about 70–90° C. and at about one atmosphere of pressure. It has also been found that the spent catalyst may be regenerated by recalcination in air at 555° C. The regenerated catalyst performs with the same selectivity and activity as virgin catalyst.

The fact that negligible amounts of the meta isomer are produced from this nitration process makes the nitro reaction product very useful as a feedstock for the manufacture of high purity DNT (dinitrotoluene) and (99.0%) TNT (2,4,6-trinitrotoluene). Not only can the mixed para and ortho isomers be nitrated to TNT; the ortho and para isomers can be separated into the individual components. For example, the mixture containing ortho and para-nitrotoluenes and having a high concentration of the para isomer, of at least about 86%, can be held under sublimation conditions to obtain a pure para nitro toluene.

While particular embodiments of the present invention have been illustrated and specifically described in this specification, it is intended that this invention includes those variations in materials temperature and conditions as would be within the skill of the art to which it is directed. It is not intended that these specific illustrations and descriptions limit the invention.

We claim:

1. A method for the nitration of substituted aromatic compounds having at least one ring activating ortho, and para directing substituent group which comprises the steps of heating said aromatic compound in the presence of a solid acidic small pore size zeolite catalyst at a temperature within the range of 70–90° C., and adding concentrated nitric nitric acid having a concentration ranging from 90–98% to the heated mixture, so resulting in a product having a high proportion of para and ortho nitro isomers.

2. Method in accordance with claim 1 wherein the aromatic compound has at least one ortho and para directing group selected from the class consisting of alkyls, oxygenated alkyl and halogens.

3. Method in accordance with claim 1 wherein the concentration of the nitric acid is 90%, by weight.

4. Method in accordance with claim 2 wherein the substituted aromatic compound is an alkyl aromatic.

5. Method in accordance with claim 2 wherein the substituted aromatic compound is toluene and the reaction products are essentially ortho and para nitrotoluene.

6. Method in accordance with claim 2 wherein the substituted aromatic compound is an alkoxy aromatic compound and the reaction product is an essentially para nitro isomer thereof.

7. Method in accordance with claim 2 wherein the substituted aromatic compound is an acyloxy aromatic compound and the reaction product is an essentially para nitro isomer thereof.

8. Method in accordance with claim 7 wherein the substituted aromatic compound is anisole and the reaction products comprise essentially para-nitromethoxyanisole.

9. Method in accordance with claim 7 wherein the substituted aromatic compound is 4-phenyl butyric acid and the reaction products are essentially 4-(4-nitrophenyl)butyric acid and 4-(2-nitrophenyl) butyric acid.

10. Method in accordance with claim 2 wherein the substituted aromatic compound is a halobenzene.

11. Method in accordance with claim 10 wherein the substituted aromatic compound is chlorobenzene and the reaction products are essentially 100% para-nitrochlorobenzene.

12. Method in accordance with claim 1 wherein the pore size of the zeolite catalyst is within the range of 5 to about 5.5 Angstroms.

13. Method in accordance with claim 1 wherein the Si to Al ratio of the zeolite catalyst is from about 120 to about 1,000.

* * * * *